United States Patent [19]

Hinrichs et al.

[11] Patent Number: 4,857,665

[45] Date of Patent: Aug. 15, 1989

[54] PROCESS FOR WORKING UP THE FILTRATION RESIDUE OF CRUDE SODIUM PREPARED BY FUSION ELECTROLYSIS INTO A HIGH-PURITY SODIUM ALCHOLATE

[75] Inventors: Walter Hinrichs, Bruehl; Herbert Hovestadt, Erftstadt; Ludwig Lange, Bruehl; Kurt A. Ruppert, Langenselbold; Erich Splett, Huerth-Berrenrath, all of Fed. Rep. of Germany

[73] Assignee: Degussa Aktiengesellschaft, Frankfurt, Fed. Rep. of Germany

[21] Appl. No.: 144,346

[22] Filed: Jan. 15, 1988

[30] Foreign Application Priority Data

Jan. 24, 1987 [DE] Fed. Rep. of Germany ........ 3702052

[51] Int. Cl.$^4$ .............................................. C07C 31/30
[52] U.S. Cl. ...................................... 568/851; 568/840
[58] Field of Search ................................. 568/851, 840

[56] References Cited

U.S. PATENT DOCUMENTS

| | | | |
|---|---|---|---|
| 2,796,443 | 6/1957 | Meyer et al. | 568/851 |
| 4,042,636 | 8/1977 | Lenz et al. | 568/851 |
| 4,150,244 | 4/1979 | Knorre et al. | 568/851 |

FOREIGN PATENT DOCUMENTS

| | | | |
|---|---|---|---|
| 0192608 | 8/1986 | European Pat. Off. | 568/851 |
| 1043309 | 11/1958 | Fed. Rep. of Germany | 568/851 |

*Primary Examiner*—Werren B. Lone
*Attorney, Agent, or Firm*—Beveridge, DeGrandi & Weilacher

[57] ABSTRACT

A process for converting the filtration residue of crude sodium produced by fusion electrolysis into a sodium alcoholate with a low NaOH content. The residue first is intensively and continuously mixed for 2–5 hours at 300–600° C. and then is added with stirring to the particular alcohol, possibly with heat added. The alcoholate solution so formed is filtered and the alcoholate may be obtained from the filtrate by distilling off the solvent.

10 Claims, No Drawings

PROCESS FOR WORKING UP THE FILTRATION RESIDUE OF CRUDE SODIUM PREPARED BY FUSION ELECTROLYSIS INTO A HIGH-PURITY SODIUM ALCHOLATE

The present invention relates to a process for converting the sodium contained in the residue accumulating when filtering liquid crude sodium obtained by fusion electrolysis into a sodium alcoholate with a low content of sodium oxide, sodium hydroxide and sodium carbonate. The sodium alcoholate is obtained in the form of a solution in the alcohol used for the conversion and can be optionally recovered in the form of the solid product in finely divided form.

The sodium prepared by fusion electrolysis at about 600° C., namely the so-called crude sodium, contains about 2% contaminations. In addition to small amounts of entrained crucible melt ($BaCl_2$, $CaCl_2$, $NaCl$) and oxides, hydroxides and carbonates of sodium, calcium is predominantly present. The calcium segregates extensively during cooling to about 120° C. and can be separated together with the remaining impurities by filtration through a steel wire netting.

As a rule, the calcium content of the so-called standard grade purified sodium is 300–600 ppm, whereas the oxide and chloride content each are less than 10 ppm. On the other hand, the filter residue, the so-called filter sludge, contains about 15–21% by weight, on the average about 17% by weight of calcium. By using a piston press with bar-sieve cylinders at pressures of 150–250 bars to press out the filter sludge, a substantial part of the sodium is recovered. As a result, the calcium content of the filter press cake obtained thereby rises to 25–33% by weight and on the average to approximately 29% by weight. The filter press cake still retaining substantial sodium is used to prepare a diluted sodium-hydroxide/calcium-hydroxide alkaline solution in a filter press cake recovery apparatus (U.S. Pat. No. 2,660,517). The alkaline solution can be used, for example, to neutralize acid waste waters.

As there is some danger in preparing a mixture of sodium-hydroxide/milk of lime from the filter press cakes and because the inevitable formation of sodium aerosols requires costly purification of the exhaust air for ecological reasons using special filter equipment such as the Brink type, efforts have been made in the past to avoid press cake recovery using costly equipment which is of low efficiency regarding the recovery of sodium, and furthermore to circumvent the problematic conversion of the press cake into the so-called press cake lye.

SUMMARY OF THE INVENTION

In accordance with the process of the present invention, the above problems are avoided in a surprising and simple manner by a targeted dissolution of residual sodium contained in the filtration residue of the fusion-electrolytically prepared crude sodium by means of alcohol, preferably methanol, according to the known reaction:

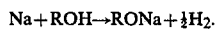

$$Na + ROH \rightarrow RONa + \tfrac{1}{2}H_2.$$

There is a large and worldwide demand for sodium alcoholates, in particular sodium methylate. For example, sodium methylate is used in the chemical industry (for instance as a condensation, esterification and trans-esterification agent), in the pharmaceutical industry (for instance as catalyst in the synthesis of sulfonamides, barbituric acid, vitamin $B_1$), in the cooking oil and fat industry (for instance to improve the dessication of plant oils) and in the detergent and lacquer industry. The compound is most widely marketed in the form of about 20–30% by weight of alcoholic solutions, wherein the admissible limits of sodium oxide, sodium hydroxide and sodium carbonate (computed a sodium hydroxide) is a maximum of 0.5% by weight.

The process of this invention is suitable both to prepare alcoholate solutions (in the alcohol corresponding to the alcoholate) and to prepare alcoholates in the form of solids.

DETAILED DESCRIPTION OF THE INVENTION

Accordingly, it is an object of the invention to provide a process for converting the sodium contained in the residue which accumulates when filtering liquid crude sodium produced by the well known fusion electrolysis process into a sodium alcoholate with a low content in sodium oxide, hydroxide and carbonate in the form of a solution in the alcohol used in the conversion and, where desired, for isolating the solid product.

It is a feature of the process of the invention that the residue containing conventional amounts of sodium, alloyed and suspended calcium, atmospherically formed sodium and calcium oxidation products and possibly also organic substances are intensively and continuously mixed under an inert gas for 2–6 hours at temperatures between 300 and 600° C. Thereafter, the product where it is used as a solid, is worked into shaped parts. Alternatively, if it is to be used as a liquid material, it is cooled while being agitated to a temperature above but fairly close to the sodium melting point and then is agitated further. The residue in the desired solid or liquid form is added with stirring to the required amount of the alcohol being considered as regards the desired end concentration of the sodium alcoholate solution. The reaction is carried out if necessary by heating, and upon termination of the reaction, the alcoholate solution is separated by filtration from the insoluble impurities. The solid alcoholate can be recovered, if desired, by distilling off the solvent vehicle which is the alcohol used in the reaction.

If organic substances are present in the residue, then advantageously, as empirically shown, it should be annealed for 3–6 hours at 400–600° C.

In accordance with the present invention, the process enables, for example, recovery of methanol solutions from calcium methylate-free sodium methylate with low content of sodium oxide, sodium hydroxide and sodium carbonate computed as NaOH, namely of less than 0.5% by weight. By distilling the alcohol solvent off, a solid product can be recovered with a residual hydroxide content computed as NaOH of less than 2% by weight. The alcoholate solutions of the invention can be prepared within the concentration range as determined by the saturation temperature. A content of 21 and 30% by weight sodium methylate is preferred for commercial purposes.

Air and humidity should be excluded from every stage of the process of this invention. For this purpose inert-gas flushing is used. Suitable inert gases are noble gases such as argon or nitrogen. In carrying out the process, the filtration residue obtained from filtering the liquid crude sodium of the fusion electrolysis and which contains about 78–84% by weight of sodium metal is used. It is essential if an alcoholate of low NaOH content is to be obtained that the prescribed temperatures and durations of treatment be observed in the presence of continuous and intensive mixing of the filter residue being thermally treated. If the thermally treated material is to be processed subsequently into shaped parts, it may be introduced cold or moderately warm (temperature between room temperature and slightly below the sodium melting point) into the alcohol which is previously placed in the vessel.

For an alternative method which is simpler in terms of technology and hence industrially preferable, temperatures not far above the sodium melting point (for instance 120° C.) are used for introduction as a fluid mass. The alcohol always is supplied in excess; the total metal content of the filter residue being processed always being totally converted for the amounts of alcohol used in preparing the alcoholate solutions.

The reaction vessel contents are kept in motion by agitation during the introduction of the sodium-containing filter residue and during the formation of the alcoholate.

When methanol for instance is used, the temperature following the introduction of the residue computed for a desired final methylate concentration rises rapidly to the methanol boiling point (64.7° C.). As the methylate concentration increases, the boiling point rises somewhat as follows:

| 10% by weight | to about 70° C.; |
| 20% by weight | to about 80° C.; |
| 30% by weight | to about 90° C. |

The vaporized methanol is condensed in a reflux condensor and runs back into the reaction vessel.

As the sodium methylate concentration rises, the reaction slows, especially if the reaction vessel is not thermally insulated, and accordingly heating is required to bring the reaction to conclusion. As a result, the reaction can be carried out in a quantitative manner.

The hydrogen which accumulates in large quantities and escapes through the reflux condenser can be captured and used alone or mixed with natural gas for heating purposes in industrial applications. Where such utilization is impossible, the hydrogen, which contains minor amounts of methanol, can be burnt off without danger.

The sodium methylate solution so obtained must now be separated from a fine gray slurry suspended in it. This slurry consists in particular of unreacted contaminations of the processed filter sludge and also of calcium methylate, formed by the reaction of the calcium metal, present in average concentrations of about 17% by weight in the filter sludge being processed, with methanol.

The separation of slurry from methylate solution is carried out by filtration, preferably by pressurized filtration. The filtrate is completely free of calcium (less than 1 ppm Ca) and on the average contains less than 0.2% by weight of undesired sodium compounds. The filtrate is completely colorless even when the filter residue used did absorb organic substances when being transferred through greased valves into the reaction vessel.

By distilling off the excess alcohol, a powdery colorless sodium methylate solid product can be obtained.

The preparation of other alcoholates can take place in corresponding manner.

The accumulating filter cake obtained in the process and which contains about 50% by weight in sodium methylate solution can be also washed with alcohol to recover the adhering alcoholate or it may be burned directly. As a result thereof, essentially CaO remains. The latter can be slaked with water into milk of lime.

The milk of lime can be used if necessary to neutralize acid plant waste waters.

The process of the invention is further illustrated below in the following examples:

EXAMPLE 1 (PREPARING A 30% SODIUM METHYLATE SOLUTION)

A filter sludge from the crude sodium filtration with a total calcium content of 17.7% by weight was used.

For the thermal treatment, a 3-liter laboratory agitator reactor made of stainless steel and with a flanged lid with agitator and with gas inlet and outlet conduits for argon flushing was used. There was deposited in the reaction tank 1.2 kg of filter sludge.

The heating was accomplished by means of a continuously adjustable heating plate. The jacket and lid of the reactor were thermally insulated with mineral wool. After the filter residue was heated to the molten condition, a blade stirrer located near the bottom and the walls of the reactor tank was agitated intensively at 150 rpm. A temperature of 500° C. was maintained for 4 hours during the agitation. Upon cooling under argon, portions of the melt were cast into a rectangular stainless steel mold 10 cm high, top: 12×32 cm, bottom: 6×32 cm, and the samples were preserved in a dry condition under an inert gas.

For the reaction of thermally pre-treated sodium filter sludge with methanol, a ground-joint apparatus was used. This consisted of a 2-liter four-neck flask with attached funnel for the methanol, a dip thermometer, a transfer tube to introduce the solid filter sludge cut into cubes about 1 cm on edge and with attached intake stubs for the inert gas, and a reflux condenser for the condensate and to evacuate the inert gas and hydrogen through a dip means in white oil (paraffin oil). The reaction mixture is agitated by a magnetic stirrer.

Because of the heavy generation of hydrogen during the reaction between sodium and methanol and further to avoid reforming sodium hydroxide and alcohol by means of atmospheric humidity, complete exclusion of air by constant flushing with inert gas was resorted to.

The following quantities were used to prepare a 30% sodium methylate solution from pure sodium when known methods are used: 1,000 ml methanol (dry, residual water content 0.013% by weight) and 115.64 g sodium.

In processing the thermally pre-treated filter sludge containing sodium, the addition of solids had to be raised to 140 g (17.7% by weight) on account of a preceding analysis of the total calcium content. Precise adjustment of the percentage of the alcoholic product solution can be carried out upon reaction termination by merely ascertaining the alkalinity of a filtered sample according to hydrolysis. Thus, if there is a finding of insufficiency, it is carried out by reloading filter sludge or by removing distillate from the reflux. If the concentration values are too high, the adjustment takes place by further addition of methanol.

In order to carry out the reaction, the filter sludge cast after the thermal pre-treatment and then solidified was quickly cut into cubes about 1 cm on the side. Then, the calculated amount (140 g/l) was weighed in and conveyed to the transfer tube and the argon flushing was commenced. While all of the equipment was being flushed to be air-free, the required amount of alcohol ($CH_3OH$) for the adjustment of the final desired concentration was admitted through the funnel into the reaction flask and the agitator was turned on. After ascertaining the absence of oxygen in the volume of the apparatus by gas analysis, the filter sludge cubes were pushed out of the transfer tube into the reaction flask. The exothermal reaction began promptly and the boiling temperature of methanol (64.7° C.) was reached soon thereafter (5 minutes). The temperature rose thereafter to 90° C. with increasing methylate concentration at 30% by weight.

It was found that the reaction with methanol becomes sluggish at higher methylate concentrations. There is a definite likelihood of the reaction essentially ceasing above about 25% by weight of methylate, and therefore less heat will be set free per unit time. This was evidenced by the temperature constantly dropping at the given heat radiation from the reaction flask being used (whereby the rate of reaction again is slowed). Therefore, the flask contents were kept at the boiling temperature by external heating using a hood heater. The total duration of the reaction as a result could be reduced to about 1½ hours.

The methylate solution so obtained is colored grey by finely dispersed insoluble substances and is highly contaminated. The finely crystalline impurities (less than 2 μm) are best separated by filtration under high pressure.

The single layer filter Merkur EF 14/2 made by Seitz Werke, Bad Kreuznach, which is designed for a maximum pressure of 3 bars was used. The free filtering area is covered with GORE-TEX membrane C and was about 150 cm². To increase the rate of filtration of the highly viscous methylate solution, it was filtered hot and the filter was heated to near the boiling point of the alcoholate solution, for example, to about 70° C. A clear and colorless filtrate could thus be obtained, even though the filter sludge that was used did contain in this case organic foreign substances in the form of lubricating grease (about 0.1% by weight).

Analysis of the sodium-methylate solution:

| | |
|---|---|
| content of $CH_3ONa$ | 30.3% |
| content of NaOH + $Na_2CO_3$ computed as NaOH | 0.19% |
| content of Ca (atomic absorption spectrograph). | less than 1 ppm |

EXAMPLE 2: (PREPARING A 20% SODIUM ETHYLATE SOLUTION)

A filter sludge from the crude sodium filtration with a total calcium content of 15.6% by weight was used.

For the preparation of a 20% sodium ethylate solution, 57.33 g of Na/1,000 ml of ethanol are required. When using and processing the sodium filter sludge of Example 1, 68.00 g of the filter sludge pretreated in this case for 6 hours at 300° C. therefore had to be added to the alcohol. The previously introduced alcohol had a residual water content of 0.07% by weight.

Analysis of the sodium ethylate solution:

| | |
|---|---|
| content of $C_2H_5ONa$ | 19.8% |
| content of NaOH + $Na_2CO_3$ calculated as NaOH | 0.37% |
| content of Ca (atomic absorption spectrograph). | 1 ppm |

EXAMPLE 3: (PREPARING A 20% SODIUM BENZYLATE SOLUTION)

Filter sludge from the crude sodium filtration with a total content of calcium of 19.2% by weight was used.

The theoretical sodium requirement in preparing a 20% sodium benzylate solution is 38.03 g Na/1,000 mol benzylalcohol. Accordingly, 47.00 g of the sodium filter sludge used in Example 1 and thermally pretreated here for 2 hours at 600° C. were used similarly to Example 1 to form the alcoholate. The benzyl alcohol used had a residual water content of 0.06% by weight.

Analysis of the sodium benzylate solution:

| | |
|---|---|
| content of $C_6H_5CH_2ONa$ | 20.3% |
| content of NaOH + $Na_2CO_3$ calculated as NaOH | 0.4% |
| content of Ca (atomic absorption spectrograph). | 4 ppm |

EXAMPLE 4: (PREPARING A 10% SODIUM PHENYLETHYLATE SOLUTION)

Filter sludge from the crude sodium filtration with a total calcium content of 18.0% by weight was used.

The theoretical sodium requirement to prepare a 10% sodium phenylethylate solution is 16.37 g Na/1,000 ml 2-phenylethanol. When using the sodium filter sludge employed in Example 1 and thermally pretreated here for 4 hours at 550° C., 20.00 g of sludge had to be added to the previously introduced alcohol with an $H_2O$ content of 0.03% by weight.

Analysis of the sodium phenylethylate solution:

| | |
|---|---|
| content of $C_6H_5CH_2CH_2ONa$ | 10.1% |
| content of NaOH + $Na_2CO_3$ calculated as NaOH | 0.35% |
| content of Ca (atomic absorption spectrograph). | 7 ppm |

Alcohols suitable for the purposes of the invention include lower aliphatic alcohols; e.g. 1 to 6 carbon atoms, and aromatic alcohols; e.g. 6 to 12 carbon atoms.

Further variations and modifications of the foregoing invention will be apparent to those skilled in the art from a reading of the above description and are intended to be encompassed by the claims appended hereto.

German priority application P 37 02 052.8-42 is relied on and incorporated by reference.

We claim:

1. A process for converting the sodium contained in the residue accumulating in the filtration of liquid crude sodium from fusion electrolysis into a sodium alcoholate with a low content of sodium oxide, sodium hydroxide and sodium carbonate in the form of a solution in said alcohol used for reacting the sodium comprising:
heating the filtration residue containing sodium, alloyed and suspended calcium, and oxidation products of sodium and calcium, under intense mixing to temperatures in the range from 300 to 600° C. for 2 to 6 hours, adding the so heat treated residue to an alcohol corresponding to the desired sodium alcoholate and being present in an amount required to achieve the desired final concentration in the solution, said alcohol being selected from the group consisting of lower aliphatic alcohols of 1 to 6 carbon atoms and aromatic alcohols of 6 to 12 carbon atoms, and separating the resulting alcoholate solution from insoluble impurities by filtering, all foregoing steps be carried out under inert gas atmosphere.

2. The process according to claim 1, wherein the heat treated intermediate product is shaped into pieces before adding it as a solid to the alcohol.

3. The process according to claim 1, wherein the heat treated intermediate product is cooled under stirring to a temperature above but near the melting point of sodium and stirring is continued for some time before adding it as a fluid mass to the alcohol.

4. The process according to claim 1, wherein solid, powdery sodium alcoholate is recovered by distilling off solvent.

5. The process according to claim 1, wherein the alcohol is a lower aliphatic alcohol of 1 to 6 carbon atoms.

6. The process according to claim 1, wherein the alcohol is methanol or ethanol.

7. The process according to claim 1, wherein the alcohol is an aromatic alcohol of 6 to 12 carbon atoms.

8. The process according to claim 7, wherein the alcohol is benzylalcohol or 2-phenylethanol.

9. The process according to claim 1, wherein the heating of the residue is carried out for 3 to 6 hours at a temperature in the range from 400 to 600° C.

10. The process according to claim 1, wherein the heat treated residue is added to the said alcohol and the resulting solution is heated to assist the reaction to form the corresponding sodium alcoholate.

* * * * *